United States Patent [19]

Biedermann

[11] Patent Number: 4,834,078

[45] Date of Patent: May 30, 1989

[54] ANKLE-JOINT ORTHOPAEDIC PROSTHESIS

[76] Inventor: Lutz Biedermann, Am Schtäfersteig 8, D-7730 VS-Villingen, Fed. Rep. of Germany

[21] Appl. No.: 162,403

[22] PCT Filed: Jan. 19, 1987

[86] PCT No.: PCT/EP87/00024

§ 371 Date: Jan. 26, 1988

§ 102(e) Date: Jan. 26, 1988

[87] PCT Pub. No.: WO87/07498

PCT Pub. Date: Dec. 17, 1987

[30] Foreign Application Priority Data

Jun. 3, 1986 [DE] Fed. Rep. of Germany ....... 3618577

[51] Int. Cl.⁴ .................................................. A61F 5/00
[52] U.S. Cl. ................... 128/80 H; 128/80 C; 128/80 F; 128/80 R
[58] Field of Search ............... 128/80 R, 80 A, 80 B, 128/80 E, 80 G, 80 H, 80 J, 80 D, 80 DB, 80 F, 80 C

[56] References Cited

U.S. PATENT DOCUMENTS

| 2,760,774 | 8/1956 | Perez | 128/80 DB |
|---|---|---|---|
| 3,732,861 | 5/1973 | Lehneis | 128/80 E |
| 3,976,059 | 8/1976 | Lonardo | 128/80 E |
| 4,006,741 | 2/1977 | Arluck | 128/90 |
| 4,136,686 | 1/1979 | Arluck | 128/90 |
| 4,169,469 | 10/1979 | Arluck | 128/90 |
| 4,289,122 | 9/1981 | Mason et al. | 128/80 E |
| 4,316,454 | 2/1982 | Perka | 128/77 |
| 4,320,748 | 3/1982 | Racette et al. | 128/80 F |
| 4,337,764 | 7/1982 | Lerman | 128/80 F |
| 4,614,181 | 9/1986 | Karlsson | 128/80 F |
| 4,638,794 | 1/1987 | Grisar | 128/80 H |
| 4,738,252 | 4/1988 | Friddle et al. | 128/80 H |

FOREIGN PATENT DOCUMENTS

| 2516945 | 11/1975 | Fed. Rep. of Germany . | |
| 3228753A1 | 2/1984 | Fed. Rep. of Germany . | |
| 2447184 | 9/1980 | France | 128/80 C |
| 0583799 | 12/1977 | U.S.S.R. | 128/80 C |

OTHER PUBLICATIONS

Berkemann et al, pp. 932-933, copy of German Abstract A61F-5/04, GM 8603420.

*Primary Examiner*—Edgar S. Burr
*Assistant Examiner*—Kimberly L. Asher
*Attorney, Agent, or Firm*—Donald Brown

[57] ABSTRACT

Ankle-joint orthopaedic prosthesis designed to provide stabilization of the tarsal joint in the case of ligament instability and to provide guidance after injuries to the ligaments, while nevertheless leaving the talocrural articulation free. It is intended to provide precise matching to the axis of the ankle-joint. The orthopaedic prosthesis (1) comprises a foot receptacle (2) and a leg receptacle (3). The foot receptacle has an opening (8) at the point corresponding to the heel walking surface. The leg receptacle has, in the triceps plantaris muscular region, a rear opening which leaves free room for the latter. The position of the point of rotation of the articulation (18, 19) linking the foot receptacle and leg receptacle can be adjusted in relation to the foot receptacle.

16 Claims, 2 Drawing Sheets

ANKLE-JOINT ORTHOPAEDIC PROSTHESIS

The present invention relates to an ankle-joint orthosis comprising a foot receptacle embracing at least partially the metatarsus and the heel, as well as a shank receptacle embracing at least partially the lower leg to be enclosed, which is connected to said foot receptacle through a joint.

From the U.S. Pat. No. 4,320,748, a foot splint is known which comprises a foot receptacle embracing the metatarsus and the heel, as well as a shank receptacle, for the stabilization of bone fractures. The shank receptacle embraces the humeral muscular apparatus so as to achieve a stabilizing effect by way of muscle abduction of the muscular apparatus of the shank. A hinge joint is provided at the foot receptacle and comprises lattice-shaped extension pieces which can be connected to the corresponding counter-piece at the shank receptacle by way of a Velcro strip fastening system. Provisions are not made for a stabilization of the pro-supination motion in the tarsal joint.

From the German utility model 86 03 420 a joint orthosis is known for supporting and guiding the tarsus, which is constituted by two lateral tongues which are interconnected through a central cross bar and wherein the ends of the tongues may be fixed at the foot, If necessary, by a bandage or Velcro strip fasteners. In this orthosis, a U-shaped foot element comprises a base plate to afford support in terms of a tilting motion. At the level of the ankle, the tongues are extended respectively by a joint element with an adjustable field of angular freedom. The extension of the joint element is connected to a lateral element.

From the German patent application No. 25 16 945 laid-open for public inspection it is known to form an orthopaedic device from thermoplastic sections of a synthetic material.

The problem underlying the present invention consists in the provision of an ankle-joint orthosis of the type described by way of introduction, which contributes to the achievment of a stabilizing effect on the tarsal joint in cases of ligament instability as well as to guidance after injuries to the ligaments, while the talocrural articulation is retained whilst the ankle-joint orthosis can be easily matched to the foot involved in a simple manner. [Translator's remark: in spite of some missing letters the text could be correctly translated.]

This problem is solved by an ankle-joint orthopaedic prosthesis of the type described by way of introduction, which employs the features in the characterizing clause of Patent claim 1. The uncovering of the walking surface of the rear section of the foot enables the user of the orthosis to come into direct contact with the shoe when stepping on the heel. This is important for the feedback for the athlete's control of his muscles. The uncovering of the bulge of the muscular region of the calf results in avoidance of any compression that would affect the muscles of the calf. Since the position of the articulation relative to the foot receptacle can be chosen it has become possible to use the position of the fulcrum for the ankle-joint orthosis such that it will match the respective foot.

Further characteristics and expedient features of the present invention will result from the description of a particular embodiment with reference to the drawing. In the drawing.

The ankle-joint orthosis 1 comprises a foot receptacle 2 and a shank receptacle 3.

Figure 1:
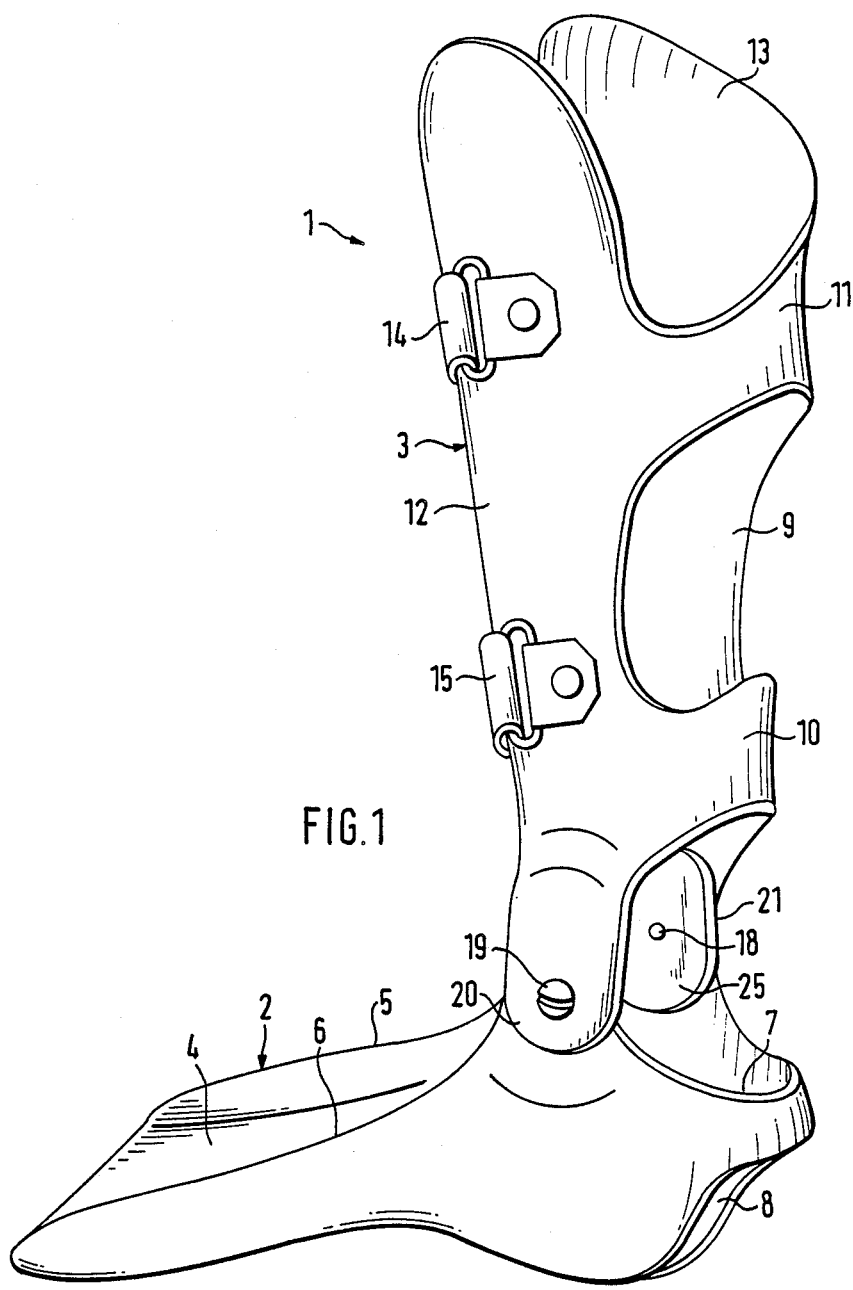
FIG. 1 is a perspective side view of an ankle-joint orthosis.
Figure 2:
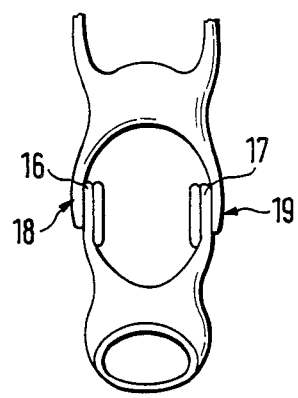
FIG. 2 is a perspective partial view seen from the front.
Figure 3:
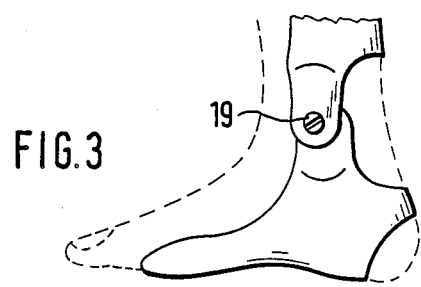
FIG. 3 is a side view wherein the foot is indicated in broken lines.

The foot receptacle 2 embraces and fixes the metatarsus in the form of a shell while addtionally the inside longitudinal arch and the front transverse arch of the metatarsus are included into the supporting action due to the envelopment by a corresponding plantar or sole zone 4 and lateral supporting zones 5, 6 integral therewith. In the heel zone, the two anatomically shaped supporting zones pass into a sufficiently raised wall 7 which affords a good embracement of the heel to be enveloped at the rear side. An opening 8 is provided at the surface where the heel protrudes; this opening is so shaped that it leaves the walking surface of the rear section of the foot free in a way that the user of the orthosis, when stepping on the heel, will have direct contact with the shoe, as can be seen best in FIG. 3.

The shank receptacle 3 is formed as a stay which embraces the shank to be received. Depending on the application, it is sufficient to embrace the shank only in part in consideration of the height of the envelopment. The illustrated embodiment is so designed that it will embrace the shank by one third of its height approximately.

The rear side of the shank receptacle 3 is so designed that an opening is provided at the location corresponding to the bulge of the muscle, while being limited by the zone 11 therebeneath. This opening is so designed that the bulge of the muscular apparatus of the calf is left uncovered and is unrestricted in motion, so that these muscles will not be affected by compression. Moreover, the shank receptacle comprises lateral side plates 12, 13 for lateral embracement of the shank, which plates are integral with the zones 10 and 11 that embrace the rear side of the shank.

At the front side, Velcro strip fasteners 14, 15 are provided so as to allow for a solid embracement of the lower leg.

In the area corresponding to the ankles of the foot to be received, the foot receptacle 2 comprises extensions 16, 17 which extend upwardly on both sides and form joint surfaces to form the respective articulations 18, 19. The shank receptacle comprises extensions 20, 21 extending downwardly, which are integral with this receptacle and form joint surfaces which are shaped so as to form an articulation in cooperation with the associated lower extension 16, 17.

Figure 4:
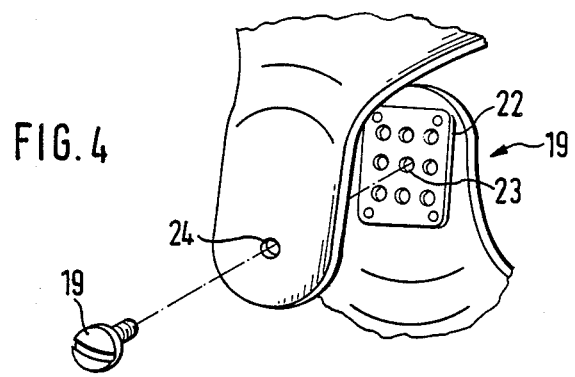
FIG. 4 is an exploded view of a joint.

As can best be seen in FIG. 4, the extensions 16, 17 of the foot receptacle comprise a base plate 22 with a plurality of holes 23 which are mutually staggered in both the vertical and the horizontal direction and which pass through the respectively associated extension. The extensions of the shank receptacle, however, are provided with a single hole 24 only. The position is adjusted by introducing the respective screws forming the pivot axes into a correspondingly chosen hole 23 of the base plate 22 and by screw-fastening them there. This produces a connection which provides for a connection of the foot receptacle with the shank receptacle which is rotatable about an axis substantially passing through the two ankles while if is fast in all other respects. A padding 25 is provided respectively at the inner side bearing against the ankles so as to improve the stabilizing effect on the foot in the orthosis.

The foot receptacle and the shank receptacle are respectively integrally made of a high-performance composite material.

The articulations 18, 19 are so designed that the angular movement between the foot receptacle and the shank zone 3 and thus the flexing and extending angle will be limited with the extent of such limitation being adjustable.

Apart from the rotation about the axis of the articulation, the foot receptacle is rigidly connected to the shank receptacle so that an exact fixing of the bone parts of the joint, i.e. the metatarsals, the ankle bone and the calcaneum on the one hand, and the fibula and tibia on the other hand, will be achieved. Due to the adjustability of the mechanical center of rotation of the articulations at several levels an exact setting of the external axis of the articulation relative to the anatomical axis of the talocrural joint can be achieved so as to avoid any incongruence. The ankle joint is freely mobile in terms of extension and flexion. The motion of the tarsus, however, in terms of pronation and supination is blocked.

I claim:

1. An ankle-joint orthosis comprising a foot receptacle embracing at least partially the metatarsus and the heel, a shank receptacle embracing at least partially the lower leg, and means comprising a joint pivotally connecting the lower end of the shank receptacle to the foot receptacle, said foot receptacle being provided with an opening at the heel end to permit the heel to contact the ground, the shank receptacle embracing the lower leg peripherally and being provided with a rear opening in the zone of the muscular area of the calf to expose the calf, said joint pivotally connecting the foot receptacle to the shank receptacle, and including means for adjusting the axis of rotation of the shank receptacle relative to the foot receptacle.

2. An ankle-joint orthosis according to claim 1, wherein the foot receptacle is provided with a plurality of staggered holes and the shank receptacle with a pin selectively engageable with the holes in the foot receptacle.

3. An ankle-joint orthosis according to claim 1, characterized in that the foot receptacle is provided with a longitudinal and transverse arch matched to the foot.

4. An ankle-joint orthosis according to claim 2, characterized in that the foot receptacle is provided with a longitudinally-transverse arch conforming to the foot.

5. An ankle-joint orthosis according to claim 1, characterized in that said joint rigidly interconnects said shank receptacle and said foot receptacle for stabilization of the prosupination motion.

6. An ankle-joint orthosis according to claim 2, characterized in that said joint rigidly interconnects said shank receptacle and said foot receptacle for stabilization of the prosupination motion.

7. An ankle-joint orthosis according to claim 3, characterized in that said joint rigidly interconnects said shank receptacle and said foot receptacle for stabilization of the prosupination motion.

8. An ankle-joint orthosis according to claim 1, characterized in that the orthosis is formed of high performance composite material.

9. An ankle-joint orthosis according to claim 2, characterized in that the orthosis is formed of high performance composite material.

10. An ankle-joint orthosis accrording to claim 3, characterized in that the orthosis is formed of high performance composite material.

11. An ankle-joint orthosis according to claim 4, characterized in that the orthosis is formed of high performance composite material.

12. An ankle-joint orthosis according to claim 1, including means for adjustment of the angle of flexion and extension.

13. An ankle-joint orthosis according to claim 2, including means for adjustment of the angle of flexion and extension.

14. An ankle-joint orthosis according to claim 3, including means for adjustment of the angle of flexion and extension.

15. An ankle-joint orthosis according to claim 4, including means for adjustment of the angle of flexion and extension.

16. An ankle-joint orthosis according to claim 5, including for adjustment of the angle of flexion and extension.

* * * * *